(12) United States Patent
Yum et al.

(10) Patent No.: US 10,603,312 B2
(45) Date of Patent: Mar. 31, 2020

(54) TRANSORAL DOSAGE FORMS COMPRISING SUFENTANIL

(71) Applicant: Durect Corporation, Cupertino, CA (US)

(72) Inventors: Su Il Yum, Los Altos, CA (US); Jaymin Shah, Sunnyvale, CA (US); Sung Yun Kwon, Fremont, CA (US); Xiaoping Song, Saratoga, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 15/870,625

(22) Filed: Jan. 12, 2018

(65) Prior Publication Data

US 2018/0228792 A1  Aug. 16, 2018

Related U.S. Application Data

(63) Continuation of application No. 14/873,066, filed on Oct. 1, 2015, now abandoned, which is a continuation of application No. 12/449,292, filed as application No. PCT/US2008/001711 on Feb. 8, 2008, now abandoned.

(60) Provisional application No. 60/904,585, filed on Mar. 2, 2007, provisional application No. 60/900,661, filed on Feb. 9, 2007.

(51) Int. Cl.
| | |
|---|---|
| *A61K 31/4535* | (2006.01) |
| *A61K 9/00* | (2006.01) |
| *A61K 9/70* | (2006.01) |
| *A61K 9/20* | (2006.01) |
| *A61K 31/485* | (2006.01) |
| *A61K 9/06* | (2006.01) |

(52) U.S. Cl.
CPC .......... *A61K 31/4535* (2013.01); *A61K 9/006* (2013.01); *A61K 9/0056* (2013.01); *A61K 9/06* (2013.01); *A61K 31/485* (2013.01); *A61K 9/2009* (2013.01); *A61K 9/2063* (2013.01); *A61K 9/7007* (2013.01)

(58) Field of Classification Search
CPC ...... A61K 31/4535; A61K 9/006; A61K 9/06; A61K 31/485; A61K 9/0056; A61K 9/2009; A61K 9/7007; A61K 9/2063
See application file for complete search history.

(56) References Cited

U.S. PATENT DOCUMENTS

| | | | |
|---|---|---|---|
| 4,671,953 A | 6/1987 | Stanley et al. | |
| 5,288,497 A | 2/1994 | Stanley et al. | |
| 5,466,464 A | 11/1995 | Masaki et al. | |
| 6,103,257 A | 8/2000 | Nisonoff | |
| 6,183,775 B1 | 2/2001 | Ventouras | |
| 6,368,625 B1 | 4/2002 | Siebert et al. | |
| 6,394,306 B1 | 5/2002 | Pawlo et al. | |
| 6,527,138 B2 | 3/2003 | Pawlo et al. | |
| 6,552,024 B1 | 4/2003 | Chen et al. | |
| 6,759,059 B1 | 7/2004 | Pettersson et al. | |
| 9,264,981 B2 | 2/2016 | Seok | |
| 2002/0160043 A1* | 10/2002 | Coleman | A61K 9/0056 424/465 |
| 2005/0042281 A1* | 2/2005 | Singh | A61K 9/0056 424/464 |
| 2005/0065175 A1 | 3/2005 | Gonzales et al. | |
| 2005/0169989 A1 | 8/2005 | Moe et al. | |
| 2007/0104763 A1 | 5/2007 | Jobdevairakkam | |

FOREIGN PATENT DOCUMENTS

| | | |
|---|---|---|
| WO | 99/24023 | 5/1999 |
| WO | 2006/097361 A1 | 9/2006 |
| WO | 2007/070632 A2 | 6/2007 |
| WO | 2007/081948 A2 | 7/2007 |
| WO | 2008/085765 | 7/2008 |

(Continued)

OTHER PUBLICATIONS

Bailey P, et al., "Difference in Magnitude and Duration of Opioid-Induced Respiratory Depression and Analgesic with Fentenyl and Sufentanil," *Anesth. Analg.* 70:8-15 (1990).

(Continued)

*Primary Examiner* — Sarah Pihonak
*Assistant Examiner* — Jason Deck
(74) *Attorney, Agent, or Firm* — Khin K. Chin; Bozicevic, Field & Francis LLP

(57) ABSTRACT

The invention pertains to methods that include administering to a subject a transoral dosage form comprising a pharmaceutical carrier and sufentanil, and maintaining a mean pH ranging from about 3.5 to about 5.5 during a dosing period after administration of the transoral dosage form as determined using an in vitro donor media test. Related dosage forms are also disclosed. Also disclosed are transoral dosage forms and related methods, wherein a transoral dosage form may comprise: (1) about 5 to about 1000 micrograms of sufentanil; (2) about 50 micrograms to about 100 milligrams of naloxone; and (3) acidifying material in an amount sufficient to provide a mean pH ranging from about 3.5 to about 5.5 during a dosing period after administration of the transoral dosage form as determined using an in vitro donor media test; wherein the dosing period begins no earlier than about 1 minute after administration of the transoral dosage form, and ends no later than about 120 minutes after administration of the transoral dosage form.

13 Claims, 9 Drawing Sheets

(56) References Cited

FOREIGN PATENT DOCUMENTS

| WO | 2009/021106 | 2/2009 |
| WO | 2010059504 | 5/2010 |

OTHER PUBLICATIONS

Bredenberg et al., "In vitro and in vivo evaluation of a new sublingual tablet system for rapid oromucosal absoroption using fentanyl citrate as the active substance," *Eur. J. Pharma. Sci.*, Nov. 2003, vol. 20, issue 3, pp. 327-334.
"Does Sufentanil Produce Less Ventilory Depression than Fentanyl," *Anesth. Analg.* 71:564-6 (1990).
Durfee S., et al., "Fentanyl Effervescent Buccal Tablets: Enhanced Buccal Absorption," *Am. J. Drug Deliv.*, 4(1): 1-5 (2006).
Emmerson PJ et al., "Binding Affinity and Selectivity of Opioids at Mu, Delta, and Kappa Receptors in Monkey Brain Membranes," *J. Pharmacol. and Exp. Therapeutics*, 271:1630-1637 (1994).
Knill "Does Sufentanil Produce Less Ventilory Depression than Fentanyl" *Anesth. Analg.* 71(5):564-6 (1990).
Kunz, KM, RN et al., "Severe Episodic Pain: Management with Sublingual Sufentanil," *J. Pain Sympt. Mgmt.* vol. 8, No. 4, p. 189-190 (1993). XP-002483916.
Niengeers, CJE et al., "Sufentanil, a very Potent and Extremely Safe Morphine-like Compound in Mice, Rats, and Dogs," Arzneim-Forsch (Drug Res.) 26:8 (1976).
Portenoy RK et al., "Breakthrough Pain: definition, prevalence, and characteristics," *Pain* 41(3):273-81 (1990).
Remington's: The Science and Practice of Pharmacy, $21^{st}$ Edition—2005. pp. 224-245.
Stanley TH et al., "Novel Delivery Systems: Oral Transmucosal and Intranasal Transmucosal," *J. Pain Sympt. Mgmt.*, vol. 7, No. 3, pp. 163-171 (1992).
International Preliminary Report on Patentability for International Application No. PCT/US2008/001711 dated Aug. 11, 2009.
International Search Report for International Application No. PCT/US2008/001711 dated Jun. 11, 2008.
Written Opinion of the International Searching Authority for International Application No. PCT/US2008/001711 dated Aug. 9, 2008.

* cited by examiner

Mean (± SD) Cumulative amounts of Sufentanil and Fentanyl permeated through pig buccal mucosa *in vitro*

Mean (± SD) Cumulative amounts of Sufentanil and Fentanyl permeated through pig buccal mucosa *in vitro*

Mean (± SD) Cumulative amounts of Sufentanil and Fentanyl permeated through pig buccal mucosa *in vitro*

TRANSORAL DOSAGE FORMS COMPRISING SUFENTANIL

This application is a continuation application of U.S. application Ser. No. 14/873,066, filed Oct. 1, 2015, which application is a continuation application of U.S. application Ser. No. 12/449,292, filed Jul. 31, 2009, which is a 371 filing of PCT/US08/01711, filed Feb. 8, 2008, which claims priority to provisional application No. 60/904,585, filed Mar. 2, 2007, and to provisional application No. 60/900,661, filed Feb. 9, 2007, all of which applications are incorporated herein by reference.

FIELD OF THE INVENTION

The invention relates to dosage forms and related methods for the treatment of breakthrough pain. More particularly, the invention relates to methods and dosage forms for transorally administering sufentanil for treatment of breakthrough pain. Further, the invention relates to transoral dosage forms and related methods wherein the transoral dosage form includes sufentanil, naloxone; and a pharmaceutical carrier.

DESCRIPTION OF RELATED ART

Millions of subjects suffer from chronic pain each year. Chronic pain includes persistent pain, which occurs more or less continuously, and breakthrough pain ("BTP"), which is transitory flares of moderate-to-severe pain in a subject whose persistent pain is otherwise controlled. BTP can reach peak intensity in as little as 3 minutes and often lasts for 30-60 minutes. BTP may occur during a specific activity, spontaneously with no apparent cause, or when the dose of the persistent pain medicine wears off.

BTP was first investigated in cancer patients, but recently researchers have found that almost an equal percentage of patients with noncancer pain suffer from BTP. An estimated 64% of all patients with cancer treated for persistent pain may experience BTP. R K Portenoy et al., "Breakthrough pain: definition, prevalence and characteristics" Pain 41(3): 273-81 (1990). Up to 74% of patients treated for persistent pain from other conditions, such as low back pain, diabetic neuropathy, and osteoarthritis may experience BTP.

Several drugs for the treatment of BTP are commercially available. ACTIQ® (oral transmucosal fentanyl citrate available from Cephalon Inc.) is approved for BTP. ACTIQ® is available in the form of a lozenge on a handle. Another such medication is FENTORA® (fentanyl buccal tablet available from Cephalon, Inc.). These medicines are designed to be fast acting, in order to be taken at the onset of BTP and to provide quick pain relief.

Despite the availability of ACTIQ® and FENTORA®, however, BTP treatment remains an unmet medical need. Many subjects with BTP cannot be adequately treated with existing medications. ACTIQ can be uncomfortable to use, as subjects suffering from pain may need to maintain the lozenge against their cheek for 15 minutes. The physical size of the lozenge and stick can create discomfort within that period, particularly if multiple doses are needed per day. Rubbing of the lozenge against the mucosal surface as suggested in the product label can irritate the mucosal surface of the subject's mouth. Additionally, adverse events related to use of fentanyl in unsupervised settings (where most BTP episodes occur) may include serious respiratory depression.

Additionally, there are concerns about diversion and subsequent abuse of BTP treatments that contain potent opioids. Abusers may obtain drugs intended for use in treating BTP, and extract the opioid from the dosage forms. The extracted opioid may be abused parenterally or by intranasal administration. Alternatively, the dosage forms may be crushed and directly intranasally administered without extraction steps. Abusers may also use other routes of administration or overdoses of the BTP drugs as part of the overall pattern of abuse.

Accordingly, new dosage forms and related methods are needed to address the problems as noted above.

BRIEF SUMMARY OF THE INVENTION

In an aspect, the invention relates to methods comprising: administering to a subject a transoral dosage form comprising a pharmaceutical carrier and sufentanil, and maintaining a mean pH ranging from about 3.5 to about 5.5 during a dosing period after administration of the transoral dosage form as determined using an in vitro donor media test.

In another aspect, the invention relates to transoral dosage forms comprising: about 5 to about 1000 micrograms of sufentanil; and acidifying material in an amount sufficient to provide a mean pH ranging from about 3.5 to about 5.5 during a dosing period after administration of the transoral dosage form as determined using an in vitro donor media test.

In an aspect, the invention relates to a method comprising: administering to a subject a transoral dosage form comprising: (1) sufentanil; (2) naloxone; and (3) a pharmaceutical carrier, and maintaining a mean pH ranging from about 3.5 to about 5.5 during a dosing period after administration of the transoral dosage form as determined using an in vitro donor media test; wherein the dosing period begins no earlier than about 1 minute after administration of the transoral dosage form, and ends no later than about 120 minutes after administration of the transoral dosage form.

In another aspect, the invention relates to a transoral dosage form comprising: (1) about 5 to about 1000 micrograms of sufentanil; (2) about 50 micrograms to about 100 milligrams of naloxone; and (3) acidifying material in an amount sufficient to provide a mean pH ranging from about 3.5 to about 5.5 during a dosing period after administration of the transoral dosage form as determined using an in vitro donor media test; wherein the dosing period begins no earlier than about 1 minute after administration of the transoral dosage form, and ends no later than about 120 minutes after administration of the transoral dosage form.

BRIEF DESCRIPTIONS OF THE SEVERAL VIEWS OF THE DRAWINGS

DETAILED DESCRIPTION OF THE INVENTION

Figure 1:
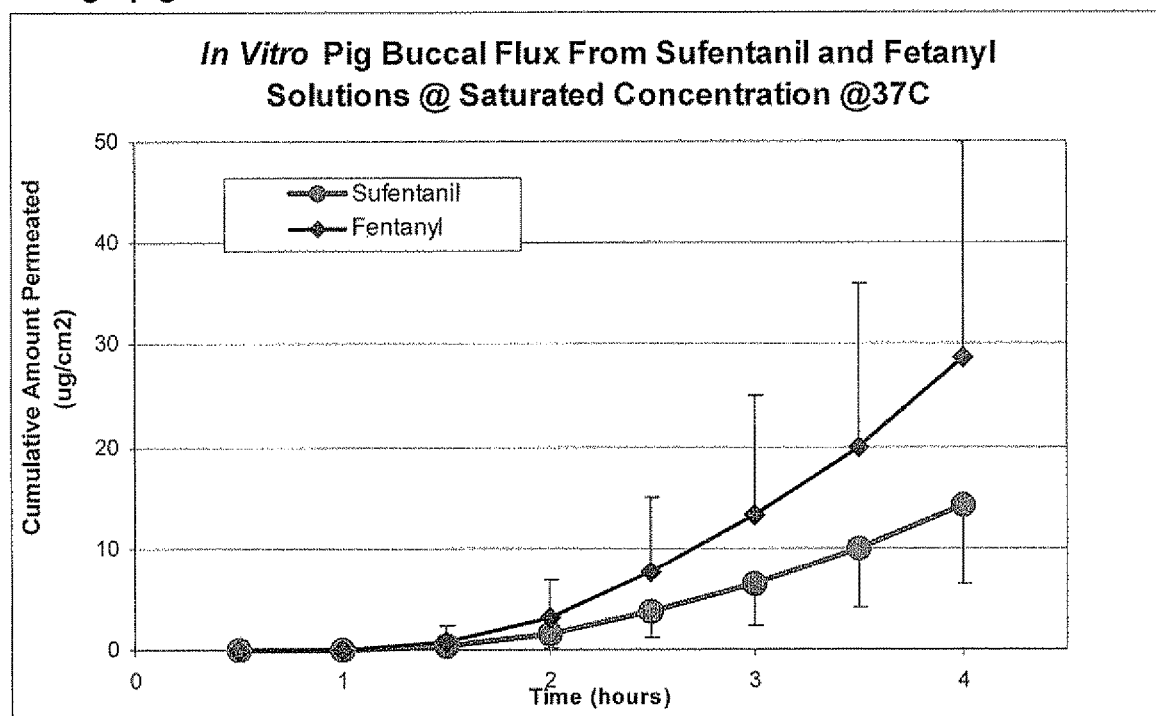
FIG. 1 shows cumulative amounts of sufentanil and fentanyl permeated through pig buccal mucosa in vitro in an embodiment disclosed in Example 2.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules, reference to "a solvent" includes a mixture of two or more such compositions, reference to "an adhesive" includes mixtures of two or more such materials, and the like.

A. INTRODUCTION

Surprisingly, the inventors have discovered that the problems in the art noted above can be addressed by providing methods that comprise administering to a subject a transoral dosage form comprising a pharmaceutical carrier and sufentanil, and maintaining a mean pH ranging from about 3.5 to about 5.5 during a dosing period following administration of the transoral dosage form to the subject, as determined using an in vitro donor media test.

Additionally, the inventors have discovered that the problems in the art noted above can be addressed by providing transoral dosage forms that comprise about 5 to about 1000 micrograms of sufentanil, expressed on the basis of converting any salt forms of sufentanil present in the transoral dosage form to the free base equivalent weight; and acidifying material in an amount sufficient to provide a mean pH ranging from about 3.5 to about 5.5 during a dosing period following administration of the transoral dosage form to a subject, as determined using an in vitro donor media test.

Further, the inventors have discovered that the problems in the art noted above can be addressed by providing methods that comprise: administering to a subject a transoral dosage form comprising: (1) sufentanil; (2) naloxone; and (3) a pharmaceutical carrier, and maintaining a mean pH ranging from about 3.5 to about 5.5 during a dosing period after administration of the transoral dosage form as determined using an in vitro donor media test; wherein the dosing period begins no earlier than about 1 minute after administration of the transoral dosage form, and ends no later than about 120 minutes after administration of the transoral dosage form.

Additionally, the inventors have discovered that the problems in the art noted above can be addressed by providing transoral dosage forms that comprise: (1) about 5 to about 1000 micrograms of sufentanil; (2) about 50 micrograms to about 100 milligrams of naloxone; and (3) acidifying material in an amount sufficient to provide a mean pH ranging from about 3.5 to about 5.5 during a dosing period after administration of the transoral dosage form as determined using an in vitro donor media test; wherein the dosing period begins no earlier than about 1 minute after administration of the transoral dosage form, and ends no later than about 120 minutes after administration of the transoral dosage form.

Combinations of a potent opioid and a potent opioid antagonist are at first not an intuitive combination for a breakthrough pain product. This is because, to be effective, BTP products comprising opioids are administered under conditions and by routes of administration such that opioids are absorbed quite quickly. Many opioid antagonists are similar in chemical structure to opioids, and therefore conditions and routes of administration that promote fast absorption of opioids also tend to lead to fast absorption of opioid antagonists. In theory, absorption of both opioids and opioid antagonists is undesirable, because the antagonists would counteract the opioid, thus leading to reduced analgesia.

It is therefore an advantage of the present invention that the inventors have identified methods and dosage forms that usefully combine sufentanil and/or pharmaceutically acceptable salts thereof with naloxone and/or pharmaceutically acceptable salts thereof. Such methods and dosage forms may demonstrate efficacy in treatment of breakthrough pain while providing abuse deterrent features.

Sufentanil and/or its pharmaceutically acceptable salts thereof is useful in the practice of the present invention. It offers several safety advantages over fentanyl, which is widely prescribed for BTP. It has been shown to have an improved safety margin over fentanyl in laboratory animals. C J E Niemegeers et al., "Sufentanil, a very Potent and Extremely Safe Morphine-like Compound in Mice, Rats, and Dogs" Arzneim.-Forsch (Drug Res) 26:8 (1976). Sufentanil may enjoy a safety margin in respiratory depression as compared to fentanyl. P. Bailet et al., "Difference in Magnitude and Duration of Opioid-Induced Respiratory Depression and Analgesia with Fentanyl and Sufentanil" Anesth. Analg. 70:8-15 (1990); but see "Does Sufentanil Produce Less Ventilory Depression Than Fentanyl" Anesth. Analg. 71:564-6 (1990). Sufentanil also has certain clinical advantages compared to other less potent opioids or analgesics because less drug needs to be absorbed by a subject to provide an efficacious concentration of sufentanil in the subject as compared to the less potent opioids or analgesics.

Naloxone, and its pharmaceutically acceptable salts, is an opioid antagonist commonly administered via the intravenous route, especially for treatment of opioid overdoses. Its oral bioavailability is quite low, potentially around 2% compared to intravenous dosing. On injection, naloxone is fast acting, often showing activity with minutes after dosing. Naloxone is fairly potent and can induce withdrawal symptoms in opioid-dependent subjects.

A useful route of administration for delivery of sufentanil is via the transoral route. The transoral route is advantageous because it avoids first-pass metabolic effects. Additionally, the transoral route may provide potentially faster absorption and distribution to the central nervous system than other routes suitable for out-patient use, i.e. non-parenteral routes such as oral, transdermal, etc. However, there are problems that have been recognized in the art with the use of transoral sufentanil.

Conventionally, sufentanil free base has been the preferred form of sufentanil used in formulations that are intended to be absorbed transorally. This is because sufentanil free base is un-ionized, and therefore may be expected to cross oral mucosal tissues more readily than ionized sufentanil. However, sufentanil free base has a very low solubility in aqueous fluids, thus significantly limiting sufentanil in solution that can permeate across oral mucosal tissues. This very low solubility results in low bioavailability of the free base.

Several attempts have been made to address this problem, including fentanyl effervescent buccal tablets that provide first a low pH environment to enhance solubility and then a high pH environment to shift the equilibrium towards the free base form of a drug. Such a system is disclosed in S. Durfee et al., "Fentanyl Effervescent Buccal Tablets: Enhanced Buccal Absorption" Am J Drug Daily 4(1):1-5 (2006) (Durfee"). Other similar systems are described in United States Published Patent Application No. 2005/0042281 of Singh et al. ("Singh").

However, such systems can create a problem when the inventive dosage form comprises both sufentanil and naloxone, and/or pharmaceutically acceptable salts of sufentanil or naloxone. As noted elsewhere, conditions that provide for enhanced absorption of sufentanil, and/or its pharmaceutically acceptable salts, also promote transoral absorption of naloxone and/or its pharmaceutically acceptable salts. Therefore, including both sufentanil and naloxone in a system such as the Durfee system would presumably lead to a poorly effective system because both the opioid and its antagonist would be absorbed.

Conversely, conditions under which naloxone would be poorly absorbed are also conditions under which sufentanil would be expected to be poorly absorbed. For instance, ionized naloxone would be expected to be poorly absorbed transorally, because ionized species tend not to be very effective at being passively transported across the oral membranes. However, at pH values where naloxone is ionized, sufentanil is also ionized. Ionized sufentanil conventionally would be expected to be poorly absorbed transorally, rendering the dosage form ineffective at treating BTP.

The inventors, however, have unexpectedly realized that sufficient ionized sufentanil can be presented for absorption from a transoral dosage form to provide an efficacious plasma concentration of sufentanil to a subject. Without wishing to be limited to a specific mechanism of action, the inventors have hypothesized that the rate limiting step for delivery of sufentanil, especially the free base, may be the initial dissolution step. Following dissolution and depending on the ambient pH, enough dissolved sufentanil free base material may exist in equilibrium with the ionized sufentanil to be absorbed across the oral mucosa and provide pain relief to a subject. What is more, sufentanil has more affinity for the mu receptor as compared to naloxone. P. J. Emmerson et al., "Binding Affinity and Selectivity of Opioids at Mu, Delta, and Kappa Receptors in Monkey Brain Membranes" J. Pharmacol. And Exp. Therapeutics 271-1630-1637 (1994). Therefore, a greater naloxone flux than sufentanil flux may be required to fully antagonize sufentanil. The methods and dosage forms of the present invention may provide conditions under which the relative fluxes of naloxone and sufentanil are such that the naloxone does not fully antagonize the sufentanil, thereby potentially preserving the efficacy of the sufentanil in treatment of BTP.

This principle is illustrated in Examples 2-4, and 6. Examples 2-4 show the results of in vitro tests that support achievement of significant sufentanil flux when the drug is presented for absorption in an ionized state, i.e. presented for absorption at a mean pH ranging from about 3.5 to about 5.5 during a dosing period following administration of the transoral dosage form to a subject, as determined using an in vitro donor media test. Example 6 uses some of this in vitro data, in comparison with other data relating to administration of sufentanil and fentanyl, to calculate the likely performance of the inventive dosage forms and methods in subjects. The results of these calculations support efficacy of the inventive dosage forms and methods, which as noted elsewhere herein is surprising in light of conventional understanding about the appropriate form of sufentanil for inclusion in a sufentanil transoral dosage form.

The inventors further recognized that there is a pH range above which absorption falls off significantly, and below which tissue damage and/or irritation may occur in a subject. Within this pH range, appropriate delivery of sufentanil occurs. This can be seen in comparing Examples 2-4 with Example 5. Example 5 shows the result of in vitro studies that suggest that at a pH=6.5, absorption of sufentanil following delivery by a transoral dosage form is likely to be less than what would be expected at lower pH such as pH=5.0 (Examples 2-4). This finding is in contrast, for instance, to the invention of Singh, described above, which is clearly intended to adjust pH to a point wherein the predominant drug species present is in the un-ionized form, i.e. a pH closer to 6.5 than to 5.0. At pH values less than 3.5, irritation of a subject's oral tissues and associated discomfort may result.

Meanwhile, the absorption of naloxone may be expected to be greatly reduced at a mean pH of about 3.5 to about 5.5 during a dosing period after administration of the transoral dosage form as determined using an in vitro donor media test. Reducing absorption of naloxone therefore reduces its negative impact on the efficacy of sufentanil in treating BTP through a transoral route of administration. Under such circumstances, the inventive methods and dosage forms provide for effective treatment of BTP with abuse deterrent features.

Various transoral dosage forms that may be useful in the practice of the present invention are illustrated in the Examples.

The invention will now be discussed in more detail.

B. DEFINITIONS

"Acidifying material" means a material that is used to lower and maintain a desired mean pH during a dosing period, as determined using an in vitro donor media test. In embodiments, acidifying agent is present in an amount sufficient to provide a mean in vitro artificial saliva pH ranging from about 3.5 to about 5.5 during a dosing period following buccal dosing of the dosage form to a subject. A pH value below about 3.5 is undesirable because of potential damage to a subject's oral tissues. A pH above about 5.5 is undesirable because of low transoral absorption, as discovered by the present inventors and discussed in more detail elsewhere herein.

In certain embodiments, the acidifying material comprises one or more buffer(s), as is described elsewhere herein.

In embodiments, the acidifying material comprises acids such as ascorbic, acetic, citric, D-gluconic, dimethylglutaric, DL-lactic, hydrochloric L-malic, fumaric, galactaric, L-lactic, L-tartaric, or succinic or combinations thereof.

"Buffer" means materials that resist change in hydronium ion and the hydroxide ion concentration (and consequent pH) upon addition of small amounts of acid or base, or upon dilution, when in solution. Buffers typically may comprise a weak acid and its conjugate base or a weak base and its conjugate acid. In certain embodiments, buffers may be used that operate to maintain the mean pH in a range from about 3.5 to about 5.5 during a dosing period, as determined by an in vitro donor media test. The amount of buffer required to achieve the desired pH range may be estimated using literature values for the buffer capacity of saliva, along with its flow rate, and/or may be established experimentally using test animals or human subjects.

In embodiments, the buffer may comprise one or more of the following weak acids (with their corresponding conjugate bases): ascorbic, acetic, citric, D-gluconic, dimethylglutaric, DL-lactic, L-malic, fumaric, galactaric, L-lactic, L-tartaric, succinic. Additional buffers are described in "Handbook of Pharmaceutical Salts—Properties, Selection, and Use" Editors: P. Heinrich Stahl and Camille G. Wermuth published by: Verlag Helvetica Chimica Acta, Zurich, Switzerland and Wiley-VCH, Weinheim, Germany (2002).

"Dosage form" means a composition suitable for pharmaceutical administration. In certain embodiments, dosage forms useful in the practice of the invention comprise transoral dosage forms. Additional information regarding dosage forms useful in the practice of the invention is found elsewhere herein.

"Dosing period" means an interval of time after administration of the inventive dosage forms. In certain embodiments, dosing periods according to the invention begin no earlier than about 1 minute after administration of the transoral dosage form, and ends no later than about 120 minutes after administration of the transoral dosage form. In other embodiments, dosing periods according to the invention begin no earlier than about 2 minutes after administration of the transoral dosage form, and ends no later than about 60 minutes after administration of the transoral dosage form. In still other embodiments, dosing periods according to the invention begin no earlier than about 2 minutes after administration of the transoral dosage form, and ends no later than about 30 minutes after administration of the transoral dosage form. In yet other embodiments, dosing periods according to the invention begin no earlier than about 3 minutes after administration of the transoral dosage form, and end no later than about 60 minutes after administration of the transoral dosage form. In further embodiments, dosing periods according to the invention begin no earlier than about 4 minutes after administration of the transoral dosage form, and ends no later than about 60 minutes after administration of the transoral dosage form. In yet further embodiments, dosing periods according to the invention begin no earlier than about 5 minutes after administration of the transoral dosage form, and end no later than about 60 minutes after administration of the transoral dosage form.

"In vitro donor media test" means an in vitro test performed generally as follows:

Fresh pig buccal tissue is cleaned in tap water at room temperature, and the muscle tissue is removed by surgical knife and scissor. The buccal tissue is cut into 1-inch circular specimens, being careful to exclude any damaged tissue areas. Next, a pre-cut buccal tissue specimen is positioned on the top edge of the receptor side of a modified glass Franz cell with the basolateral side of the buccal tissue facing the receptor chamber. The dosage form being tested may be applied at this point, or may be added once the cell assembly is substantially complete, depending on the nature of the dosage form (transoral dosage forms having a fixed drug releasing area may be applied either before or after assembly of the cell, while transoral dosage forms having a variable drug releasing area are preferably added after assembly of the cell). The donor side of the Franz cell is securely positioned over the buccal tissue/system assembly, and fitted with a plastic cap to avoid evaporation of the donor solution. The receptor chamber is filled with citrate buffer at pH 5.0 and is constantly stirred, @ approximately 400 rpm, with the use of a Teflon coated magnetic spin bar. The permeation cell is equilibrated at 37° C. in a circulating water bath for the duration of the experiment. The receptor volume is 6.9 ml. A substantially infinite sink condition is maintained in the receptor chamber for the duration of the experiment. Either 1 or 2 milliliters of deionized water are added to the donor compartment. The choice of either 1 or 2 ml of water depends on the volume, composition, etc., of the dosage form used. Generally, larger dosage forms may require use of 2 ml of water to completely cover such dosage forms. No agitation of the donor side media is performed following administration of the dosage form.

Addition of the water to the dosage form in the donor compartment, or addition of the dosage form to the water-containing donor compartment comprises administration of the dosage form for the purposes of determining pH during the dosing period for the present invention.

The pH of the donor media may be determined during the appropriate dosing period using pH paper or an electronic pH probe. In a preferred embodiment, an electronic pH probe is preferred. In embodiments, the pH determined using the in vitro test ranges from about 3.5 to about 5.5, preferably from about 4.5 to about 5.5. The purpose of the in vitro donor media test is to model what the pH of a subject's mouth might be without needing to actually measure the pH in the subject's mouth. The inventors believe that the in vitro donor media test is reflective of what happens in vivo, and usefully reflects in vivo performance of the claimed invention.

"Maintaining" means to keep a physical property within certain values.

"Mean" means the average of multiple values.

"Naloxone" means 17-allyl-4,5α-epoxy-3,14-dihydroxymorphinan-6-one (CAS Number 465-65-6, also referred to as "naloxone free base") and/or pharmaceutically acceptable salts thereof.

"Permeation enhancer" means a substance selected to promote greater transoral flux of un-ionized and/or ionized sufentanil. Examples of permeation enhancers include, but are not limited to, ethanol, polyethylene glycols, lauryl alcohol, oleyl alcohol, eucalyptol, menthol, methyl salicylate, thymol, propylene glycol, propylene glycol monocaprylate, oleoyl macrogol 6 glycerides, linoleoyl macro 6 glycerides, caprylocaproyl, macrogol 8 glycerides, propylene glycol monolaurate, polyglyeryl 6 dioleate, and diethlene glycol monoethylether, and combinations thereof. In embodiments, permeation enhancers are included in the inventive dosage forms and/or methods in amounts effective to enhance the transoral flux of un-ionized and/or ionized sufentanil. In preferable embodiments, permeation enhancers may be present in an amount ranging from about 0.1 to about 40 wt % based on the total dosage form weight. Certain lipophilic permeation enhancers useful in the practice of this invention are available from Gattefosse (Paramus, N.J.).

"Pharmaceutical carrier" means a pharmaceutically acceptable material that is pharmacologically inactive with respect to pain relief. In embodiments, pharmaceutical carriers may comprise a main vehicle (such as water, non-aqueous solvent, or combinations thereof), one or more gelling agents, one or more acidifying agents, optional permeation enhancers, and other optional pharmaceutical excipients such as flavorants, colorants, preservatives, and the like.

"Pharmaceutically acceptable salt thereof" means salts of sufentanil suitable for pharmaceutical administration. Useful salts might comprise acetate, bitartrate, chloride, citrate, fumarate, gluconate, hydrobromide, lactate, maleate, phosphate or acid phosphate, sulfate, and tartrate salts, and similar acid addition salts and combinations thereof. In a preferred embodiment, a pharmaceutically acceptable salt of sunfentanil comprises sufentanil citrate. In a preferred embodiment, a pharmaceutically acceptable salt of naloxone comprises naloxone hydrochloride.

"Subject" is used interchangeably with "individual" and means any human with which it is desired to practice the present invention. The term "subject" does not denote a particular age, and the present systems are thus suited for use with subjects of any age, such as infant, adolescent, adult and senior aged subjects In certain embodiments, a subject may comprise a patient.

"Sufentanil" means N-[4-(methoxymethyl)-1-(2-thiophen-2-ylethyl)-4-piperidyl]-N-phenyl-propanamide (CAS Number 56030-54-7, also referred to as "sufentanil free base") and/or pharmaceutically acceptable salts thereof.

"Transoral" means administration across surfaces of a subject's oral cavity, including across buccal surfaces, sublingual surfaces, and lingual surfaces.

C. DOSAGE FORMS AND ADMINISTRATION

A wide variety of dosage forms may be used in the practice of this invention. These dosage forms can generally be categorized into two main categories: transoral dosage forms having a fixed drug releasing area, and transoral dosage forms having a variable drug releasing area.

In embodiments, transoral dosage forms having a fixed drug releasing area include, but are not limited to, buccal adhesive tablets, buccal adhesive patches, and sublingual adhesive tablets. Specific embodiments of such transoral dosage forms having a fixed drug releasing area are disclosed, in part, in U.S. Pat. Nos. 5,288,497; 6,103,257; 6,183,775; 6,368,625; and 6,552,024.

In other embodiments, transoral dosage forms having a variable drug releasing area include, but are not limited to, fast dissolving tablets, fast dissolving wafers or strips, gels, buccal sprays, and liquid dosage forms. Transoral dosage forms having a variable drug releasing area useful in the practice of the invention may be obtained from Adhesives Research (Glen Rock, Pa., fast dissolving wafer), and LTS Lohmann (West Caldwell, N.J., fast dissolving wafer), and are disclosed in U.S. Pat. No. 5,466,464 assigned to Yamanouchi Inc.

In each instance, these transoral dosage forms need to be adapted by the appropriate addition of acidifying agents according to the invention to provide for the desired pH during the dosing period following administration. Further examples of dosage forms generally useful in the practice of the invention may be found in *Remington: The Science & Practice of Pharmacy*, 21$^{st}$ edition (2005), see esp. Part 5.

In certain embodiments, the inventive transoral dosage forms comprise gel dosage forms. Inventive gel dosage forms may comprise sufentanil, naloxone (in certain embodiments, while other embodiments are contemplated as being free or substantially free from naloxone), and pharmaceutical carriers that may comprise a main vehicle (such as water, non-aqueous solvent, or combinations thereof), one or more gelling agents, one or more acidifying agents, optional permeation enhancers, and other optional pharmaceutical excipients such as flavorants, colorants, preservatives, and the like. Suitable non-aqueous solvents comprise alcohols (such as ethanol), caprylic capric triglyceride, propylene glycol caprylate/caprate, propylene glycol laurate, glyceryl monolinoleate, glyceryl mono oleate/linoleate, glyceryl monooleate, propylene glycol monocaprylate, oleoyl macrogol 6 glycerides, linoleoyl macro 6 glycerides, caprylocaproyl macrogol 8 glycerides, propylene glycol monolaurate, polyglyeryl 6 dioleate, and diethlene glycol monoethylether, and combinations thereof.

Gelling agents useful in the practice of this invention include but are not limited to: cellulose ether polymers such as hydroxyethyl cellulose, hydroxypropyl cellulose, hydroxypropylmethyl cellulose (e.g. HPMC K4M and HPMC K100M), hydroxyethylmethyl cellulose; polyvinyl alcohol; polyethylene glycol; polyvinyl alcohol-polyethylene glycol graft copolymers (e.g. Kollicoat® IR); Carbopol® polymers (polyacrylic acids); carboxmethylcellulose, or polyalkylene oxides such as polyethylene oxide.

The total concentration of gelling agents in the gel dosage form ranges from about 0 to about 80 weight percent, preferably from about 1 to about 60 weight percent, and more preferably from about 1 to about 50 weight percent, based on total weight of the gel dosage form. The amount of gelling agent used depends on the type of gelling agent and targeted viscosity and hence wetting and spreading (extents and kinetics) of the gel on oral cavity tissues. More than one gelling agents can be used in order to achieve desired effects on wetting and spreading efficiency of the gel dosage form. In certain embodiments, the inventive gel dosage forms have a range of viscosity from 1-5000 cP at 37 Deg C. and contact angles ranging from 0-30 degrees on a low energy surfaces such as oral cavity tissues (10-50 dynes/cm).

In embodiments, the amount and nature of the acidifying agent(s) to be used in manufacture of the inventive gel dosage forms is determined such that a mean pH ranging from about 3.5 to about 5.5, or preferably a mean pH ranging from about 4.5 to about 5.5, is maintained during a dosing period following administration of the gel dosage form as determined using an in vitro donor media test. Formulation optimization for determining the amount and nature of the acidifying agent(s) to be used may be based on parameters such as the amount of sufentanil, or sufentanil and naloxone, present in the dosage form, the nature and amount of pharmaceutical carriers in the dosage forms, estimated saliva amount (approximately 5 ml as an initial estimate), flow rates (approximately 0.5 ml/minute as an initial estimate), and pH (estimated saliva pH is about 7.4), drug solubility—pH relationship, and the relative contribution of ionized and versus non-ionized species of sufentanil and/or naloxone to over-all sufentanil and/or naloxone flux through the transoral route.

In certain circumstances, sufentanil or naloxone may cause "dry mouth" symptoms. If this is a concern, osmotic agents such as sodium chloride and or glycerine can be added to the inventive dosage forms. Such osmotically active materials will enhance salivation and hence help maintain pH in a required range in a subject's mouth following administration.

The amount of sufentanil or pharmaceutically active salts thereof may vary, according to the amount of drug desired to be dosed. In preferred embodiments, the inventive dosage forms comprise from about 5 micrograms to about 1000 micrograms of sufentanil or pharmaceutically active salts thereof, expressed on the basis of converting any salt forms of sufentanil present in the dosage form to the free base equivalent weight. In certain preferred embodiments, the dosage form may comprise about 10, about 20, about 40, about 60, about 80, or about 100 micrograms of sufentanil or pharmaceutically active salts thereof, expressed on the basis of converting any salt forms of sufentanil present in the dosage form to the free base equivalent weight.

The amount of naloxone present in the inventive transoral dosage forms may vary, according to the amount of naloxone desired to be dosed. In preferred embodiments, the inventive dosage forms comprise from about 50 micrograms to about 100 milligrams of naloxone, expressed on the basis of converting any salt forms of naloxone present in the dosage form to the free base equivalent weight. In certain preferred embodiments, the dosage form may comprise from about 100 micrograms to about 50 milligrams of naloxone, more preferably from about 100 micrograms to about 10 milligrams of naloxone, and even more preferably from about 100 micrograms to about 5 milligrams of naloxone, expressed on the basis of converting any salt forms of naloxone present in the dosage form to the free base equivalent weight.

The inventive dosage forms may be administered conventionally, according to the nature of each dosage form. Typically, the subject will self-administer an inventive dosage form on the occurrence of BTP, which is a preferred method of administration.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing description. Such modifications and variations are intended to fall within the scope of the appended claims. The present invention is to be limited only by the terms of the appended claims, along with the full scope of equivalents to which such claims are entitled.

D. EXAMPLES

Below are examples of specific embodiments for carrying out the present invention. The examples are offered for illustrative purposes only, and are not intended to limit the scope of the present invention in any way.

Example 1: Sufentanil and Fentanyl Solutions

Excess sufentanil base and fentanyl base were added to pH 5 citric acid buffers made up in deionized water to make stock solutions of sufentanil citrate and fentanyl citrate. The stock solutions were equilibrated overnight @37° C., and the solution concentrations of drug were estimated to be at saturation, e.g. sufentanil (4.76 mg/ml) and fentanyl (17.35 mg/ml) @37° C. The stock solutions were iteratively titrated to the desired test pH of pH 5.0 with 0.1M of citric acid solution prior to being used experimentally; pH was not further measured during the permeation studies in the Examples below.

Example 2: In Vitro Evaluation of Permeability of Sufentanil and Fentanyl Through Pig Buccal Mucosal Tissue In-vitro permeation buccal flux studies were conducted with fresh pig buccal tissue. Prior to the in vitro buccal flux experiment, the buccal tissue was cleaned in tap water at room temperature, and the muscle tissue was removed by surgical knife and scissor. The buccal tissue was cut into 1-inch circular specimens, being careful to exclude any damaged tissue areas.

Next, a pre-cut buccal tissue specimen was positioned on the top edge of the receptor side of a modified Franz cell with the basolateral side of the buccal tissue facing the receptor chamber. The donor side of the Franz Cell was securely positioned over the skin/system assembly, and fitted with a plastic cap to avoid evaporation of the donor solution. The receptor chamber was filled with citrate buffer at pH 5.0 and was constantly stirred, @ approximately 400 rpm, with the use of a Teflon coated magnetic spin bar. The permeation cell was equilibrated at 37° C. in a circulating water bath for the duration of the experiment. The receptor volume was 6.9 ml. A substantially infinite sink condition was generally maintained in the receptor chamber for the duration of the experiment.

The donor side of the cell was filled (approximately 1 ml) with a donor solution that comprised the stock fentanyl or sufentanil solution, prepared according to Example 1.

At predetermined intervals (30 min, 1 hour, 1.5 hour, 2 hour, 2.5 hour, 3 hour and 3.5 hour and 4 hour), the entire receptor solution was collected from the permeation cell and refilled with fresh receptor medium. The receptor solutions were assayed for sufentanil or fentanyl content using an HPLC chromatographic method. The cumulative amounts delivered were calculated, as the sufentanil or fentanyl free base, for each cell assembly.

The results are shown in Table 1 and FIG. 1. Three test cells were averaged at each time point to arrive at the reported values.

TABLE 1

| | Mean (±SD) Cumulative Amount Permeated through pig buccal mucosa ($\mu g/cm^2$) @ 37° C. | | | | | | | |
|---|---|---|---|---|---|---|---|---|
| Drugs | 0.5 (h) | 1 (h) | 1.5 (h) | 2 (h) | 2.5 (h) | 3 (h) | 3.5 (h) | 4 (h) |
| Sufentanil | 0.0 ± 0.0 | 0.0 ± 0.0 | 0.5 ± 0.6 | 1.6 ± 1.3 | 3.7 ± 2.6 | 6.5 ± 4.1 | 9.9 ± 5.7 | 14.2 ± 7.7 |
| Fentanyl | 0.0 ± 0.0 | 0.0 ± 0.0 | 0.8 ± 1.5 | 3.1 ± 3.7 | 7.6 ± 7.5 | 13.3 ± 11.7 | 19.9 ± 16.1 | 28.7 ± 21.4 |

Figure 2:
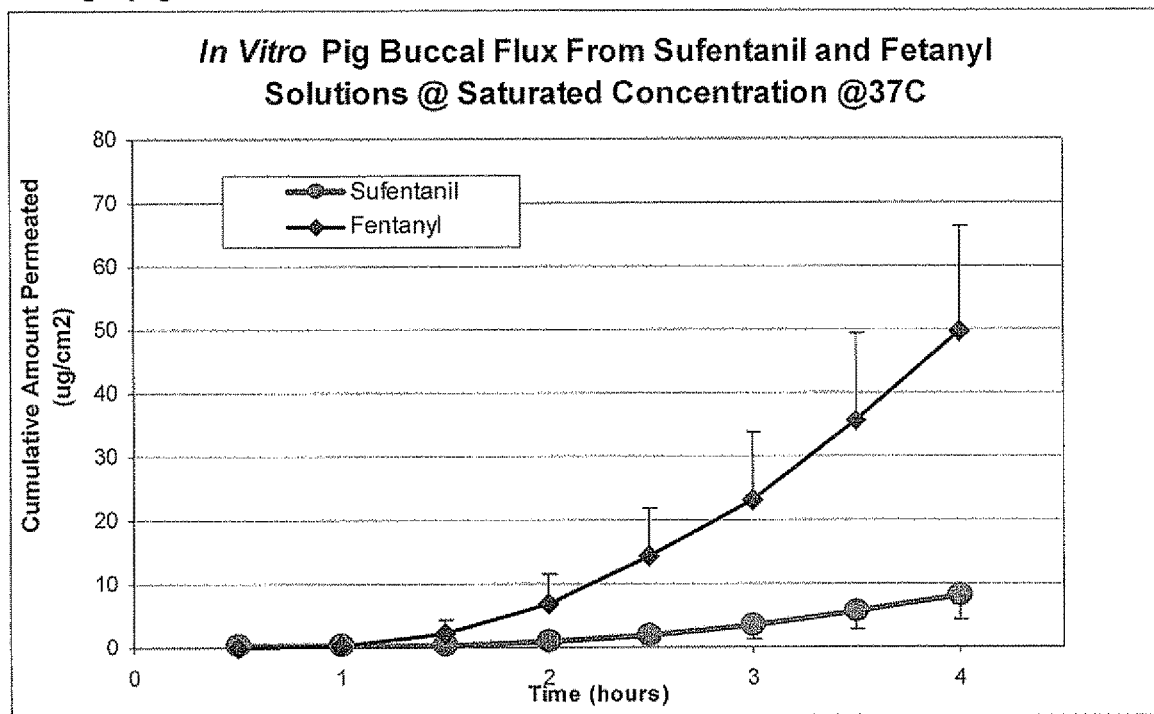
FIG. 2 shows cumulative amounts of sufentanil and fentanyl permeated through pig buccal mucosa in vitro in an embodiment disclosed in Example 3.

Example 3: In Vitro Evaluation of Permeability of Sufentanil and Fentanyl Through Pig Buccal Mucosal Tissue Example 2 was repeated, using different porcine buccal tissue samples. The results are shown in Table 2 and FIG. 2. Three test cells were averaged at each time point to arrive at the reported values.

TABLE 2

Mean (±SD) Cumulative Amount Permeated through pig buccal mucosa ($\mu g/cm^2$) @ 37° C.

| Drugs | 0.5 (h) | 1 (h) | 1.5 (h) | 2 (h) | 2.5 (h) | 3 (h) | 3.5 (h) | 4 (h) |
|---|---|---|---|---|---|---|---|---|
| Sufentanil | 0.2 ± 0.3 | 0.2 ± 0.3 | 0.3 ± 0.3 | 0.8 ± 0.5 | 1.9 ± 1.2 | 3.4 ± 2.0 | 5.6 ± 2.9 | 8.3 ± 3.9 |
| Fentanyl | 0.0 ± 0.0 | 0.4 ± 0.7 | 2.1 ± 2.4 | 6.8 ± 4.7 | 14.4 ± 7.5 | 23.2 ± 10.5 | 35.6 ± 13.7 | 49.6 ± 16.6 |

Figure 3:
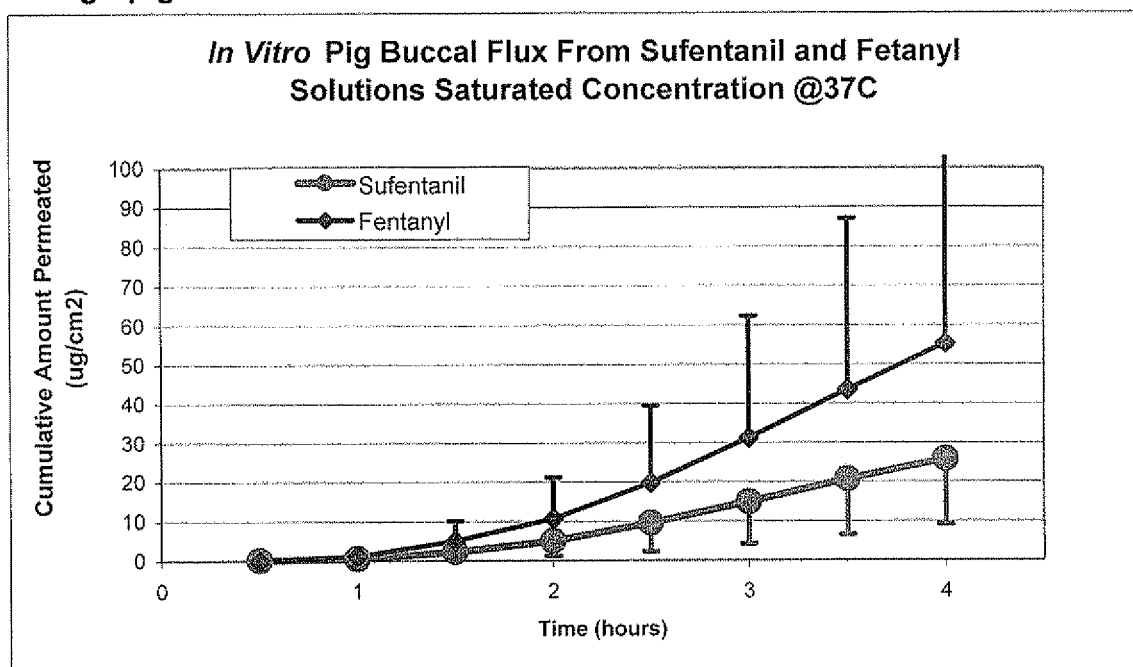
FIG. 3 shows cumulative amounts of sufentanil and fentanyl permeated through pig buccal mucosa in vitro in an embodiment disclosed in Example 4.

Example 4: In Vitro Evaluation of Permeability of Sufentanil and Fentanyl Through Pig Buccal Mucosal Tissue Example 2 was repeated, using different porcine buccal tissue samples. The results are shown in Table 3 and FIG. 3. Three test cells were averaged at each time point to arrive at the reported values.

The in-vitro skin-flux data of fentanyl and sufentanil through porcine buccal tissue was obtained in Example 2 above.

An assumption was made that the in vitro data of Example 2 represent the in-vivo input data (absorption) and based on the total amount delivered over 4 hour period, cumulative % unabsorbed vs. time plot is generated as shown below, the

TABLE 3

Mean (±SD) Cumulative Amount Permeated through pig buccal mucosa ($\mu g/cm^2$) @ 37° C.

| | 0.5 (h) | 1 (h) | 1.5 (h) | 2 (h) | 2.5 (h) | 3 (h) | 3.5 (h) | 4 (h) |
|---|---|---|---|---|---|---|---|---|
| Sufentanil | 0.2 ± 0.3 | 0.6 ± 0.3 | 2.3 ± 1.7 | 5.0 ± 3.8 | 9.5 ± 7.2 | 14.9 ± 10.7 | 20.6 ± 14.1 | 25.8 ± 16.7 |
| Fentanyl | 0.0 ± 0.0 | 1.2 ± 2.1 | 5.1 ± 6.7 | 10.6 ± 11.6 | 19.8 ± 18.2 | 31.2 ± 26.0 | 43.5 ± 33.7 | 55.3 ± 41.1 |

Figure 4:
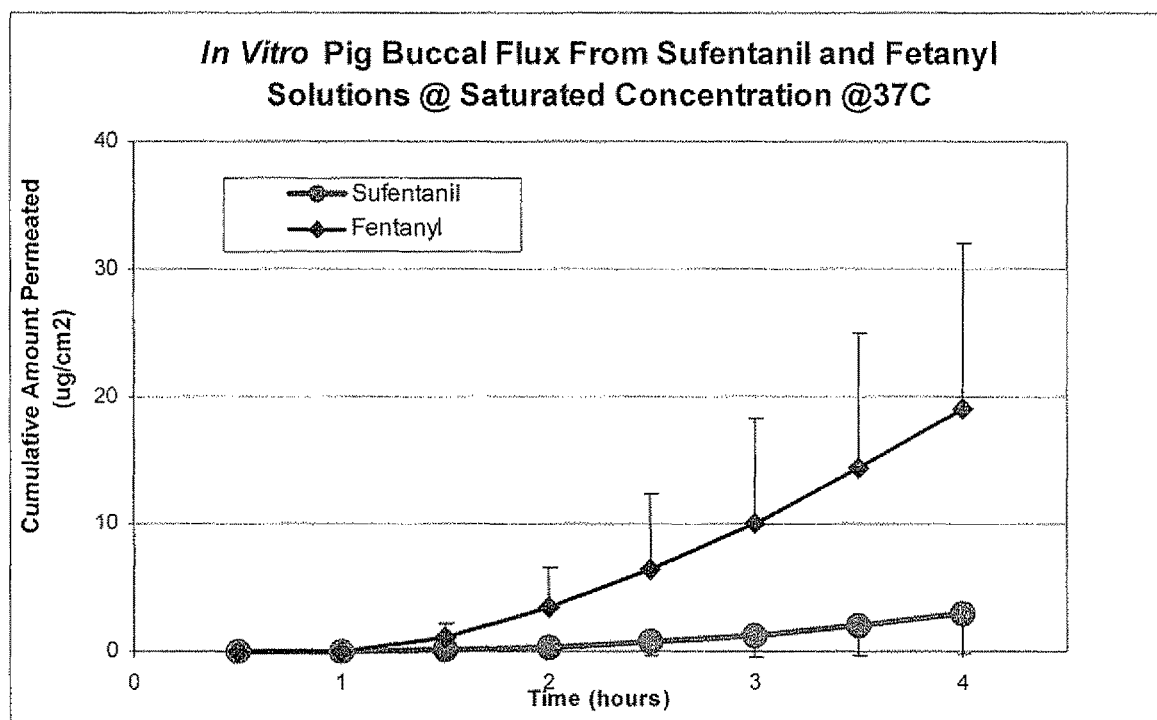
FIG. 4 shows cumulative amounts of sufentanil and fentanyl permeated through pig buccal mucosa in vitro in an embodiment disclosed in Example 5.
Figure 5:
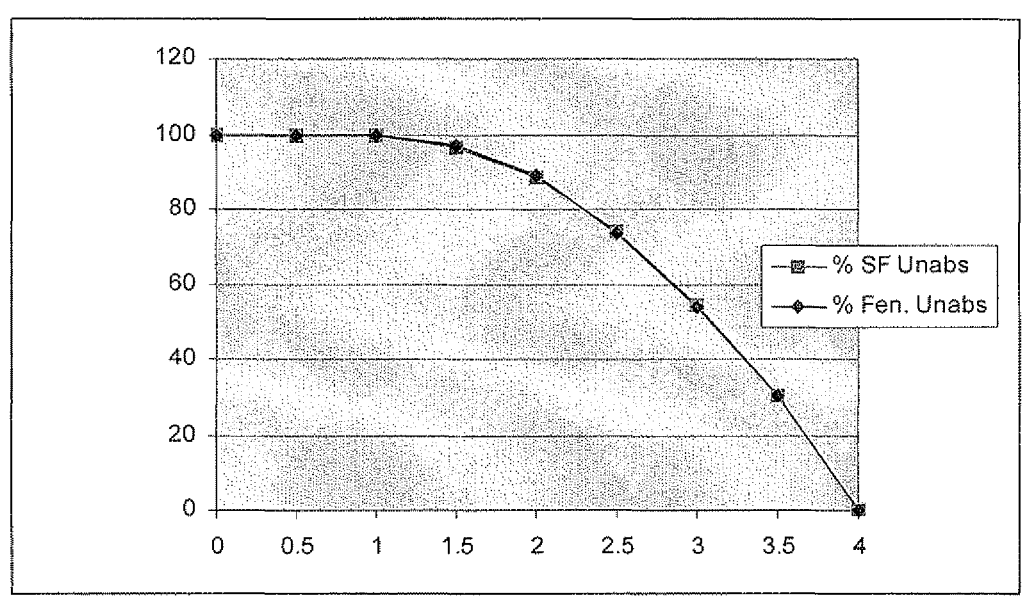
FIG. 5 shows the cumulative % drug unabsorbed vs. time, based on in vitro data from Example 2.
Figure 6:
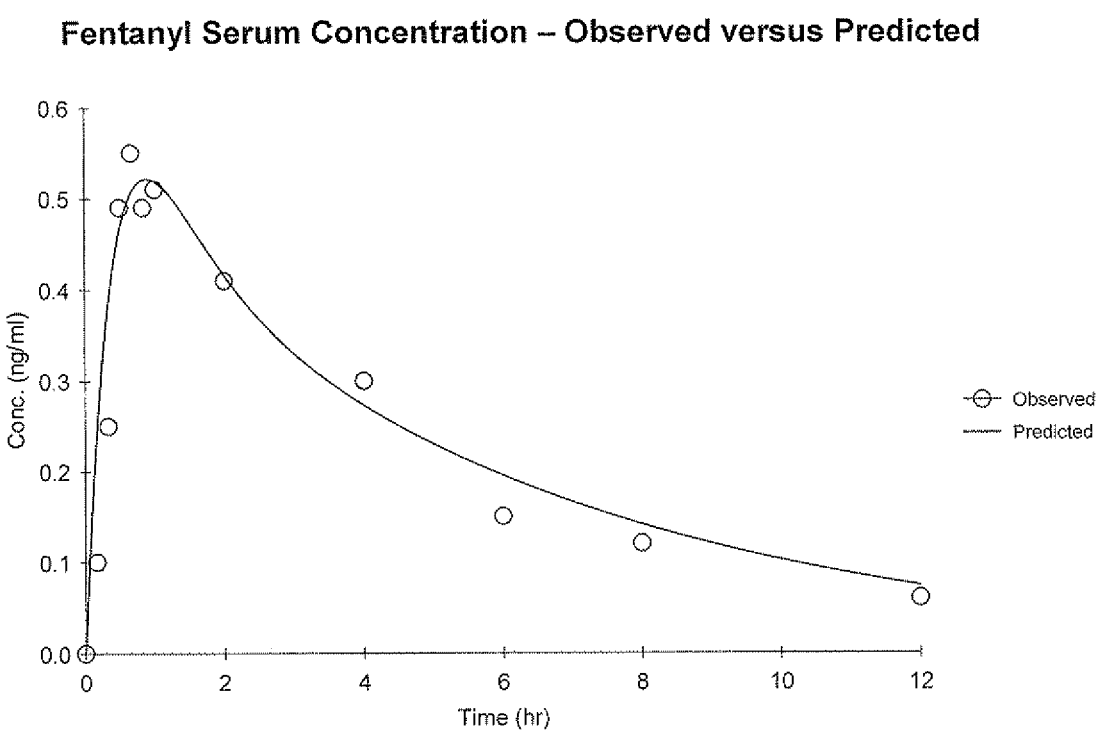
FIG. 6 shows fentanyl serum concentrations, including observed versus predicted values, for a fetanyl effervescent buccal tablet.
Figure 7:
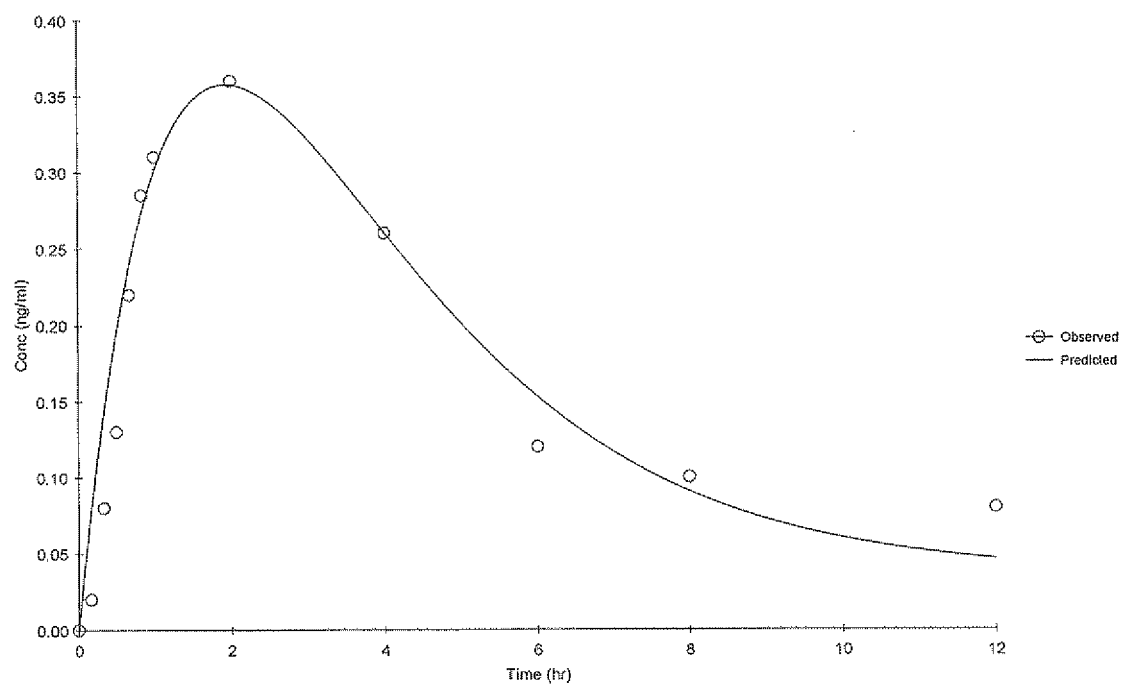
FIG. 7 shows the model fit for a fentanyl buccal tablet.
Figure 8:
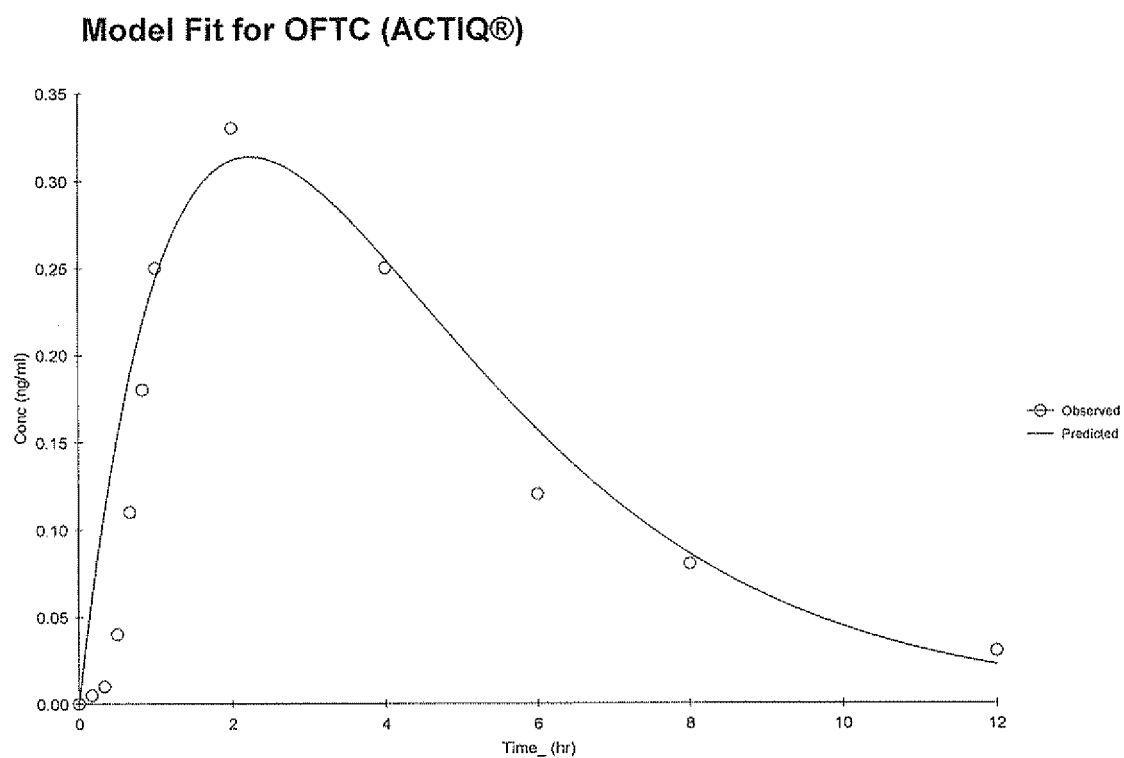
FIG. 8 shows the model fit for an oral transmucosal fentanyl citrate dosage form (ACTIQ®).
Figure 9:
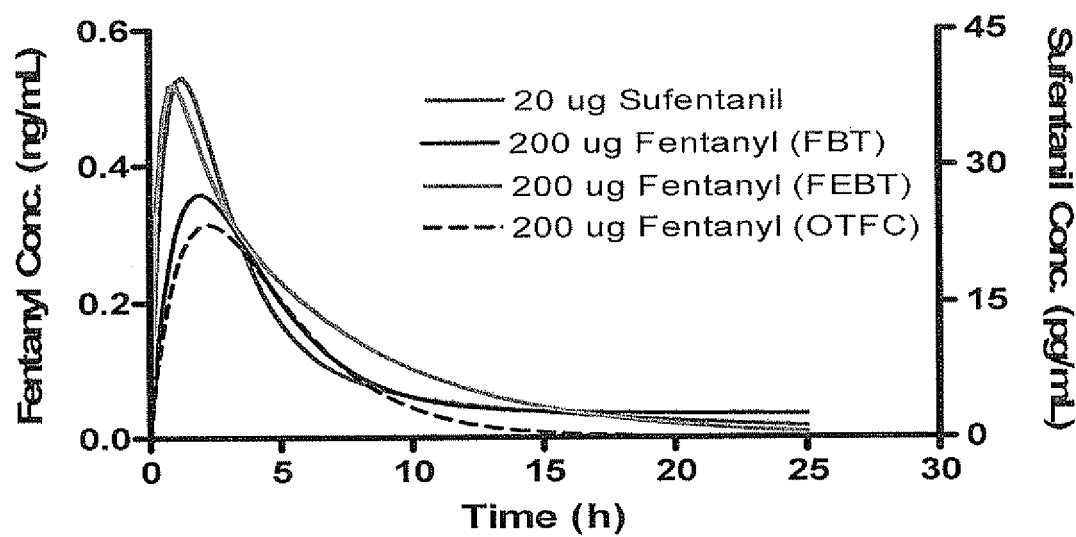
FIG. 9 shows predicted drug concentration from model fit and in-vitro flux.

Example 2 was repeated, using different porcine buccal tissue samples. Additionally, the pH of the donor solutions according to Example 1 were adjusted to a pH of 6.5 prior to starting the studies, rather than a pH of 5.0. The results are shown in Table 4 and FIG. 4. Three test cells were averaged at each time point to arrive at the reported values.

log slope of these lines served as an estimate of 'Ka' for sufentanil and fentanyl of 0.555 and 0.553 $hr^{-1}$, respectively.

Next, fentanyl serum concentration data following a 200 μg dose of a fentanyl effervescent buccal tablet ("FEBT"), commercialized as FENTORA® (available from Cephalon Pharmaceuticals) published by Durfee were fitted to a 2

TABLE 4

Mean (±SD) Cumulative Amount Permeated through pig buccal mucosa ($\mu g/cm^2$) @ 37° C.

| 0.5 (h) | 1 (h) | 1.5 (h) | 2 (h) | 2.5 (h) | 3 (h) | 3.5 (h) | 4 (h) |
|---|---|---|---|---|---|---|---|
| 0.0 ± 0.0 | 0.0 ± 0.0 | 0.1 ± 0.2 | 0.3 ± 0.6 | 0.8 ± 1.1 | 1.3 ± 1.8 | 2.1 ± 2.5 | 3.0 ± 3.2 |
| 0.0 ± 0.0 | 0.0 ± 0.0 | 1.1 ± 1.1 | 3.4 ± 3.2 | 6.4 ± 5.9 | 10.1 ± 8.1 | 14.4 ± 10.6 | 19.1 ± 13.0 |

Example 5: Prediction of In Vivo Sufentanil Profile from In Vitro Buccal Flux Data Pharmacokinetics of sufentanil plasma concentrations was predictively modeled from the data obtained in Examples 2-4 in 4 steps: (1) disposition parameters of sufentanil were ascertained; (2) the in vitro data from Example 2 were used to estimate the predictive absorption rate constant (Ka) using the Wagner-Nelson method, (3) fentanyl disposition parameters were calculated using the literature serum concentration data of Durfee et al. "Fentanyl Effervescent Buccal Tablets: Enhanced Buccal Absorption" *Am. J. Drug Deliv.* 4(1):1-5 (2006) ("Durfee"); and (4) using the skin flux predicted 'Ka' values and the disposition parameters of fentanyl and sufentanil, respective concentrations were predicted.

The disposition parameters of sufentanil used in the predictive modelling were as follows:
V1=144,586.060232 milliliters
K21=0.241440 $hr^{-1}$
Alpha=1.730311 $hr^{-1}$
Beta=0.144651 $hr^{-1}$ compartment pharmacokinetic model. The model fit is presented below with a very good fit of the observed and the model predicted data and the $R^2$ of 0.9488 (unweighted) and 0.9178 (weighted).

The estimated intercompartmental transfer rate constants are:

Ka=2.05 $hr^{-1}$, $K_{10}$=0.278 $hr^{-1}$, $K_{12}$=0.511 $hr^{-1}$, $K_{21}$=0.872 $hr^{-1}$.

TABLE 5

PK Parameters for FEBT

| Parameters | Literature Reported | Model Predicted |
|---|---|---|
| Cmax (ng/mL) | 0.64 ± 0.28 | 0.521 |
| Tmax (hr) | 0.5 | 0.887 |
| $AUC_t$ (ng*hr/mL) | 2.66 ± 0.63 | 2.61 |

For an non-effervescent fentanyl tablet (FBT), as reported in Durfee, 200 μg dose data was also model fitted as shown below to derive the disposition parameters. As can be observed the non-effervescent tablet had delayed and lower $C_{max}$ as compared to the effervescent tablet.

The estimated Ka value for fentanyl from the model fit is 0.615 hr$^{-1}$ very similar to the value observed from the in-vitro skin flux data seen in Example 2 of 0.553 hr$^{-1}$. A comparison between PK parameters based on observed and model fitted data is presented below:

TABLE 6

PK Parameters for FBT

| Parameters | Literature Reported | Model Predicted |
| --- | --- | --- |
| Cmax (ng/mL) | 0.40 ± 0.07 | 0.36 |
| Tmax (hr) | 2.0 | 1.932 |
| AUC$_t$ (ng*hr/mL) | 2.04 ± 0.87 | 2.06 |

Next, using the data published by Durfee, fentanyl serum concentration data following a 200 μg dose of oral transmucosal fentanyl citrate ("OTFC", formulated as ACTIQ® from Cephalon Inc.) was also model fitted as shown below.

Next, using Ka of 0.555 hr$^{-1}$ for sufentanil and 0.553 and 2.05 hr$^{-1}$ for fentanyl, the single dose drug concentrations were predicted for transoral delivery.

Some relevant predicted pharmacokinetic parameters are as presented in Table 7:

TABLE 7

| | Tmax (h) | Cmax |
| --- | --- | --- |
| SF | 1.21 | 39.79 pg/mL |
| FEBT | 0.88 | 0.521 ng/mL |
| FBT | 1.93 | 0.358 ng/mL |
| OTFC | 2.24 | 0.314 ng/mL |

Examples 6-8: Transoral Gel Dosage Forms (Prophetic)

In examples 6-8, appropriate amounts of starting materials are combined to yield inventive dosage forms having the ingredient concentrations set forth in tabular form in Table 8. The pH of the formulation is adjusted to 3.5 to 5.5 with acid or base. Sufentanil citrate and Naloxone hydrochloride are incorporated into the gel formulation as an aqueous form. Mixing is maintained until batch is homogeneous.

TABLE 8

| | Weight % | | |
| --- | --- | --- | --- |
| Ingredient | Ex. 7 | Ex. 8 | Ex. 9 |
| Hydroxyethyl cellulose | — | — | 2 |
| Hydroxypropyl cellulose | — | — | — |
| Hydroxypropylmethyl cellulose (HPMC K4M) | — | .3 | — |
| Hydroxypropylmethyl cellulose (HPMC K100M) | — | .7 | — |
| Polyvinyl alcohol | .5 | .5 | — |
| PVA-PEG graft co-polymer Kollicoat ® IR | — | — | 12 |
| Sweet peppermint | — | — | 1 |
| Sufentanil citrate | .03 | .03 | 0.03 |
| Naloxone Hydrochloride | .19 | .19 | 0.19 |
| Purified water | 4.28 | 7.28 | 84.78 |

Examples 9-11: Transoral Fast Dissolving Film Dosage Forms (Prophetic)

In examples 9-11, the method of formulation preparation for Example 6 is used with the amounts of starting materials chosen to yield well-mixed compositions having the ingredient concentrations set forth in Table 9. The pH of the formulation is adjusted to 3.5 to 5.5 with acid or base. A solvent casting method is used for manufacturing the film dosage forms according to the invention. The homogeneous mixture is cast onto a smooth surface such as the non-siliconized side of a polyester film release liner. The film is then dried under aeration at a temperature between 60° C.-80° C. The dry film formed by this process is a glossy stand alone, self-supporting, non-tacky and flexible film. The film then may be cut into a suitable shape and surface area using a cutting die to give a single dosage unit containing a dosage of sufentanil, expressed as the free base equivalent, in the range of 10-100 micrograms. The films ultimately may be packaged into a single pouch package, multi-unit blister card or multiple unit dispensers such as those disclosed in U.S. Pat. No. 6,394,306 or U.S. patent application Ser. No. 10/122,808.

TABLE 9

| | Weight % | | |
| --- | --- | --- | --- |
| Ingredient | Ex. 10 | Ex. 11 | Ex. 12 |
| Hydroxyethyl cellulose | 4 | — | 4.5 |
| Hydroxypropyl cellulose | 3 | — | — |
| Hydroxypropylmethyl cellulose (HPMC K4M) | — | 0.5 | — |
| Hydroxypropylmethyl cellulose (HPMC K100M) | — | 1 | — |
| Polyvinyl alcohol | 0.5 | 0.5 | — |
| PVA-PEG graft co-polymer Kollicoat ® IR | — | — | 15 |
| Sweet peppermint | 1 | 1 | 1 |
| Sufentanil citrate | 0.03 | 0.03 | 0.06 |
| Naloxone Hydrochloride | 0.19 | 0.19 | 0.38 |
| FD & C yellow #5 lake | 0.05 | 0.05 | 0.05 |
| Purified water | 91.23 | 96.73 | 79.01 |

Example 12: Buccal Tablets (Prophetic)

Example 2 of U.S. Pat. No. 5,288,497 is modified as follows to make a transoral dosage form according to the invention.

Sufentanil citrate is incorporated into a dissolvable matrix form. Gelatin is selected as the dissolvable matrix material.

A suitable mixture is prepared by combining the following ingredients as follows:

| Ingredient | % | grams |
| --- | --- | --- |
| sufentanil citrate | 0.005% | 0.001 |
| naloxone hydrochloride | 0.0315 | 0.0063 |
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |

-continued

| Ingredient | % | grams |
|---|---|---|
| wild cherry microcaps | 3% | 0.6 |
| peppermint microcaps | 3% | 0.6 |
| gelatin | 76.9635% | 15.3927 |
| TOTAL | 100% | 20 |

The ingredients are combined in a mixer in such a fashion as to ensure a uniform distribution of all ingredients within the mixture. Aliquots of 2 grams each are then formed by dehydration. The procedure results in the preparation of 10 oral transmucosal dosage-forms, each containing 100 micrograms of sufentanil citrate and 633 micrograms of naloxone hydrochloride. It is appreciated that similar dosage-forms may be produced using other dissolvable matrix materials such as fats, waxes (natural or synthetic), proteins, hydrogels, dissolvable resins, or other suitable dissolvable matrix materials.

Examples 13-15: Transoral Gel Dosage Forms (Prophetic)

In examples 13-15, appropriate amounts of starting materials are combined to yield inventive dosage forms having the ingredient concentrations set forth in tabular form in Table 10. The pH of the formulation is adjusted by citric acid into a range of pH of about 3.5 to about 5.5. Sufentanil citrate is incorporated into the gel formulation as an aqueous form. Mixing is maintained until batch is homogeneous.

TABLE 10

| | Weight % | | |
|---|---|---|---|
| Ingredient | Ex. 14 | Ex. 15 | Ex. 16 |
| Hydroxyethyl cellulose | 2 | — | 2 |
| Hydroxypropyl cellulose | 2 | — | — |
| Hydroxypropylmethyl cellulose (HPMC K4M) | — | 0.3 | — |
| Hydroxypropylmethyl cellulose (HPMC K100M) | — | 0.7 | — |
| Polyvinyl alcohol | 0.5 | 0.5 | — |
| PVA-PEG graft co-polymer Kollicoat ® IR | — | — | 12 |
| Sweet peppermint | 1 | 1 | 1 |
| Citric add | 0.1 | 0.1 | 0.1 |
| Sufentanil free base | 0.01 | 0.01 | 0.01 |
| Purified water | 94.39 | 97.39 | 84.89 |

Examples 16-18: Transoral Fast Dissolving Film Dosage Forms (Prophetic)

In examples 16-18, the method of formulation preparation for Example 5 is used with the amounts of starting materials chosen to yield well-mixed compositions having the ingredient concentrations set forth in Table 11. The pH of the formulation is adjusted by citric acid to 3.5-5.5. A solvent casting method is used for manufacturing the film dosage forms according to the invention. The homogeneous mixture is cast onto a smooth surface such as the non-siliconized side of a polyester film release liner. The film is then dried under aeration at a temperature between 60° C.-80° C. The dry film formed by this process is a glossy stand alone, self-supporting, non-tacky and flexible film. The film then may be cut into a suitable shape and surface area using a cutting die to give a single dosage unit containing a dosage of sufentanil, expressed as the free base equivalent, in the range of 10-100 micrograms. The films ultimately may be packaged into a single pouch package, multi-unit blister card or multiple unit dispensers such as those disclosed in U.S. Pat. No. 6,394,306 or U.S. patent application Ser. No. 10/122,808.

TABLE 11

| | Weight % | | |
|---|---|---|---|
| Ingredient | Ex. 17 | Ex. 18 | Ex. 19 |
| Hydroxyethyl cellulose | 4 | — | 4.5 |
| Hydroxypropyl cellulose | 3 | — | — |
| Hydroxypropylmethyl cellulose (HPMC K4M) | — | 0.5 | — |
| Hydroxypropylmethyl cellulose (HPMC K100M) | — | 1 | — |
| Polyvinyl alcohol | 0.5 | 0.5 | — |
| PVA-PEG graft co-polymer Kollicoat ® IR | — | — | 15 |
| Sweet peppermint | 1 | 1 | 1 |
| Citric acid | 0.1 | 0.1 | 0.1 |
| Sufentanil free base | 0.01 | 0.01 | 0.02 |
| FD & C yellow #5 lake | 0.05 | 0.05 | 0.05 |
| Purified water | 91.34 | 96.84 | 79.33 |

Example 19: Buccal Tablets (Prophetic)

Example 2 of U.S. Pat. No. 5,288,497 is modified as follows to make a transoral dosage form according to the invention.

Sufentanil citrate is incorporated into a dissolvable matrix form. Gelatin is selected as the dissolvable matrix material.

A suitable mixture is prepared by combining the following ingredients as follows:

| sufentanil citrate | 0.005% | 0.001 |
| citric acid | 1% | 0.2 |
| ribotide | 2% | 0.4 |
| compritol 888 | 2% | 0.4 |
| aspartame | 2% | 0.4 |
| vanilla microcaps | 5% | 1.0 |
| vanilla cream microcaps | 5% | 1.0 |
| wild cherry microcaps | 3% | 0.6 |
| peppermint microcaps | 3% | 0.6 |
| gelatin | 76.995% | 15.399 |
| TOTAL | 100% | 20 |

The ingredients are combined in a mixer in such a fashion as to ensure a uniform distribution of all ingredients within the mixture. Aliquots of 2 grams each are then formed by dehydration. The procedure results in the preparation of 10 oral transmucosal dosage-forms, each containing 100 micrograms of sufentanil citrate. It is appreciated that similar dosage-forms may be produced using other dissolvable matrix materials such as fats, waxes (natural or synthetic), proteins, hydrogels, dissolvable resins, or other suitable dissolvable matrix materials.

What is claimed is:

1. A method comprising:
    administering to a subject a transoral dosage form comprising a pharmaceutical carrier and sufentanil citrate, and
    maintaining a mean pH ranging from about 3.5 to about 5.5 during a dosing period after administration of the transoral dosage form as determined using an in vitro donor media test;

wherein the dosing period begins no earlier than about 1 minute after administration of the transoral dosage form, and ends no later than about 120 minutes after administration of the transoral dosage form.

2. The method of claim 1, wherein the dosing period begins no earlier than about 2 minutes after administration of the transoral dosage form, and ends no later than about 60 minutes after administration of the transoral dosage form.

3. The method of claim 2, wherein the dosing period begins no earlier than about 2 minutes after administration of the transoral dosage form, and ends no later than about 30 minutes after administration of the transoral dosage form.

4. The method of claim 1, wherein the dosing period begins no earlier than about 3 minutes after administration of the transoral dosage form, and ends no later than about 60 minutes after administration of the transoral dosage form.

5. The method of claim 4, wherein the dosing period begins no earlier than about 4 minutes after administration of the transoral dosage form, and ends no later than about 60 minutes after administration of the transoral dosage form.

6. The method of claim 5, wherein the dosing period begins no earlier than about 5 minutes after administration of the transoral dosage form, and ends no later than about 60 minutes after administration of the transoral dosage form.

7. The method of claim 1, wherein the transoral dosage form comprises a transoral dosage form having a fixed drug releasing area.

8. The method of claim 1, wherein the transoral dosage form comprises a transoral dosage form having a variable drug releasing area.

9. The method of claim 1, wherein the transoral dosage form comprises a gel dosage form.

10. The method of claim 1, wherein the mean pH is maintained in a range from about 4.5 to about 5.5.

11. The method of claim 1, wherein the transoral dosage form comprises an acidifying agent that operates to maintain the mean pH in a range from about 3.5 to about 5.5 during the dosing period, as determined using an in vitro donor media test.

12. The method of claim 11, wherein the acidifying agent comprises a buffer.

13. The method of claim 1, wherein the pharmaceutical carrier comprises one or more permeation enhancers.

* * * * *